(12) United States Patent
Inoue et al.

(10) Patent No.: US 9,796,959 B2
(45) Date of Patent: Oct. 24, 2017

(54) METHOD FOR INDUCING ASTROCYTES

(71) Applicant: KYOTO UNIVERSITY, Kyoto-shi, Kyoto (JP)

(72) Inventors: Haruhisa Inoue, Kyoto (JP); Takayuki Kondo, Kyoto (JP)

(73) Assignee: KYOTO UNIVERSITY, Kyoto-shi, Kyoto (JP)

( * ) Notice: Subject to any disclaimer, the term of this patent is extended or adjusted under 35 U.S.C. 154(b) by 0 days.

(21) Appl. No.: 14/758,185

(22) PCT Filed: Dec. 27, 2013

(86) PCT No.: PCT/JP2013/085347
§ 371 (c)(1),
(2) Date: Jun. 26, 2015

(87) PCT Pub. No.: WO2014/104409
PCT Pub. Date: Jul. 3, 2014

(65) Prior Publication Data
US 2015/0353888 A1 Dec. 10, 2015

Related U.S. Application Data

(60) Provisional application No. 61/746,788, filed on Dec. 28, 2012.

(51) Int. Cl.
*C12N 5/00* (2006.01)
*C12N 5/079* (2010.01)
*C12N 5/0797* (2010.01)

(52) U.S. Cl.
CPC ......... *C12N 5/0622* (2013.01); *C12N 5/0623* (2013.01); *C12N 2501/13* (2013.01); *C12N 2502/081* (2013.01); *C12N 2506/08* (2013.01); *C12N 2506/45* (2013.01); *C12N 2509/00* (2013.01)

(58) Field of Classification Search
None
See application file for complete search history.

(56) References Cited

U.S. PATENT DOCUMENTS

| 2002/0009743 A1 | 1/2002 | Carpenter |
| 2008/0044901 A1 | 2/2008 | Sasai et al. |
| 2015/0064734 A1 | 3/2015 | Inoue et al. |

FOREIGN PATENT DOCUMENTS

| JP | 2003-533224 A | 11/2003 |
| WO | WO 2005/123902 A1 | 12/2005 |
| WO | WO 2011/074690 A1 | 6/2011 |
| WO | WO 2013/140927 A1 | 9/2013 |

OTHER PUBLICATIONS

Friede RL, J Cell Biol, 20:Jan. 5-15, 1964.*
Munoz et al., Veterinarni Medicina, 56:231-242, 2011.*
Morizane et al., J Neurosci Res, 89:117-126, published online Dec. 8, 2010.*
International Search Report and Written Opinion of the International Searching Authority for International Application No. PCT/JP2013/085347, mailed on Apr. 1, 2014, in 7 pages.
Egawa et al., "Drug Screening for ALS Using Patient-Specific Induced Pluripotent Stem Cells," *Science Translational Medicine*, vol. 4, p. 47-54 (2012).
Foo et al., "Development of a Method for the Purification and Culture of Rodent Astrocytes," *Neuron*, vol. 71, pp. 799-811 (Sep. 8, 2011).
Johnson et al., "Functional Neural Development from Human Embryonic Stem Cells: Accelerated Synaptic Activity via Astrocyte Coculture," *The Journal of Neuroscience*, vol. 27(12), pp. 3069-3077 (Mar. 21, 2007).
Kondo et al., "Cellular Replacement Therapy in Neurodegenerative Diseases Using Induced Pluripotent Stem Cells," *Stem Cells and Cancer Stem Cells*, vol. 2, Chapter 25, pp. 241-247 (2012).
Krencik et al., "Specification of transplantable astroglial subtypes from human pluripotent stem cells," *nature biotechnology*, vol. 29(6), pp. 528-534 (Jun. 2011).
Lippmann et al., "Derivation of blood-brain barrier endothelial cells from human pluripotent stem cells," *nature biotechnology*, vol. 30(8), pp. 783-791 (2012).
Rothstein et al., "Knockout of Glutamate Transporters Reveals a Major Role for Astroglial Transport in Excitotoxicity and Clearance of Glutamate," *Neuron*, vol. 16, pp. 675-686 (Mar. 1996).
Silva et al., "A novel and rapid method for culturing pure rat spinal cord astrocytes on untreated glass," *Journal of Neuroscience Methods*, vol. 30, pp. 75-79 (1998).
Extended European Search Report issued in European Patent Application No. 13869653.9, on Jun. 27, 2016.
Gingras et al., "Optimized protocols for isolation of primary motor neurons, astrocytes and microglia from embryonic mouse spinal cord," *Journal of Neuroscience Methods*, vol. 163, pp. 111-118 (2007).
Office Action issued in corresponding Japanese Patent Application No. 2015-532199, mailed on May 17, 2016.
Krencik et al., "Directed differentiation of functional astroglial subtypes from human pluripotent stem cells," *Nature Protocols*, vol. 6(11), pp. 1710-1717 (2011).
Silva et al., "A novel and rapid method for culturing pure rat spinal cord astrocytes on untreated glass," *Journal of Neuroscience Methods*, vol. 80, pp. 75-79 (1998).

* cited by examiner

*Primary Examiner* — Kimberly A. Ballard
*Assistant Examiner* — Stacey MacFarlane
(74) *Attorney, Agent, or Firm* — Knobbe, Martens, Olson & Bear LLP

(57) ABSTRACT

The present invention provides a method for producing astrocytes from neural progenitor cells, the method comprising: (1) culturing neural progenitor cells in a culture medium comprising a neurotrophic factor; (2) dissociating the cells obtained in the step (1); and (3) subjecting the cells obtained in the step (2) to adherent culture in a culture medium comprising a neurotrophic factor using an uncoated culture vessel.

16 Claims, 4 Drawing Sheets

METHOD FOR INDUCING ASTROCYTES

CROSS-REFERENCE TO RELATED APPLICATIONS

This application is the U.S. National Phase under 35 U.S.C. §371 of International Application PCT/JP2013/085347, filed Dec. 27, 2013, which claims priority to US Provisional Applicant No. 61/746,788, filed Dec. 28, 2012.

TECHNICAL FIELD

The present invention relates to a method for producing astrocytes from neural progenitor cells derived from pluripotent stem cells. The present invention also relates to a method for selectively culturing astrocytes from a cell population comprising neurons and astrocytes.

BACKGROUND ART

Astrocytes are the most predominant cell species in the brain, and their role is said to be as important as the role of neurons. Embryologically, immature astrocytes are indispensable for formation of functional synapses (Johnson, M. A et al., J. Neurosci. 2007, 27, 3069-3077), and mature astrocytes have a capacity to block synapses and to remove excess transmitters (Rothstein, J. D et al., Neuron, 1996, 16, 675-686). Further, for maintaining nerve fibers, astrocytes play a role as supporting cells. Further, it is suggested that astrocytes may be contributing to maintenance of the function to close the blood-brain barrier by contacting their processes to the blood vessel basement membrane.

On the other hand, it is thought that abnormality of astrocytes is involved in astrocytoma, epilepsy, Alexander disease and neurodegeretative diseases. Therefore, elucidation of these diseased states by analysis of astrocytes is expected.

A method for inducing astrocytes via neural stem cells from pluripotent stem cells such as ES cells or iPS cells has been reported so far (Krencik R, et al., Nat Biotechnol. 2011, 29, 528-534).

SUMMARY OF THE INVENTION

The present invention aims to provide a novel method for producing astrocytes from neural progenitor cells. The present invention also aims to provide a method for selectively culturing astrocytes from a cell population comprising neurons and astrocytes, by utilization of the property of astrocytes to adhere to uncoated culture vessels.

As a result of intensive study to solve the above problem, the present inventors first discovered that, by utilizing the property of astrocytes to adhere to uncoated culture vessels, differentiation into astrocytes can be highly efficiently induced from neural progenitor cells prepared without carrying out a selection step, thereby completed the present invention.

It is one aspect of the present invention is to provide a method for producing astrocytes, comprising the steps:

(1) culturing neural progenitor cells in a culture medium comprising a neurotrophic factor;

(2) dissociating the cells obtained in the step (1); and (3) subjecting the cells obtained in the step (2) to adherent culture in a culture medium comprising a neurotrophic factor using an uncoated culture vessel.

It is another aspect of the present invention is to provide the method as described above, wherein said neurotrophic factor is a factor selected from the group consisting of GDNF, BDNF and NT-3.

It is another aspect of the present invention is to provide the method as described above, further comprising the steps:

(4) dissociating the cells obtained in the step (3); and (5) subjecting the cells obtained in the step (4) to adherent culture in a culture medium that does not contain a factor selected from the group consisting of GDNF, BDNF and NT-3 using an uncoated culture vessel.

It is another aspect of the present invention is to provide the method as described above, further comprising repeating, at least twice, dissociating the cells obtained in the step (5) and then subjecting the dissociated cells to adherent culture in a culture medium that does not contain a factor selected from the group consisting of GDNF, BDNF and NT-3 using an uncoated culture vessel.

It is another aspect of the present invention is to provide the method as described above, further comprising:

(6) dissociating the cells obtained in the step (5); and (7) subjecting the cells obtained in the step (6) to adherent culture in a culture medium that does not contain a factor selected from the group consisting of GDNF, BDNF and NT-3 using a gelatin-coated culture vessel.

It is another aspect of the present invention is to provide the method as described above, wherein the culture is carried out for not less than 66 days in the step (1).

It is another aspect of the present invention is to provide the method as described above, wherein the culture is carried out for not less than 30 days in the step (3).

It is another aspect of the present invention is to provide the method as described above, wherein the culture is carried out for not less than 20 days in the step (5).

It is another aspect of the present invention is to provide the method as described above, wherein said neural progenitor cells are cells produced by culturing pluripotent stem cells in a culture medium comprising a BMP inhibitor and a TGFβ inhibitor.

It is another aspect of the present invention is to provide the method as described above, wherein said BMP inhibitor is Dorsomorphin and said TGFβ inhibitor is SB431542.

It is another aspect of the present invention is to provide the method as described above, wherein said step of producing neural progenitor cells from pluripotent stem cells comprises forming an embryoid body/bodies and then subjecting the embryoid body/bodies to adherent culture.

It is another aspect of the present invention is to provide the method as described above, wherein said neural progenitor cells are human neural progenitor cells.

It is another aspect of the present invention is to provide an astrocyte produced by the method as described above.

It is another aspect of the present invention is to provide a method for selectively culturing astrocytes in a cell population comprising neurons and astrocytes, comprising:

(I) dissociating the cell population; and (II) culturing the cells obtained in the step (I) using an uncoated culture vessel.

It is another aspect of the present invention is to provide the method as described above, wherein, in the step (II), the cells obtained in the step (I) are subjected to adherent culture in a culture medium comprising a neurotrophic factor.

It is another aspect of the present invention is to provide the method as described above, further comprising:

(III) dissociating the cells obtained in the step (II); and (IV) subjecting the cells obtained in the step (III) to adherent culture in a culture medium that does not contain a factor selected from the group consisting of GDNF, BDNF and NT-3 using an uncoated culture vessel.

It is another aspect of the present invention is to provide the method as described above, further comprising repeating, at least twice, dissociating the cells obtained in the step (IV) and then subjecting the dissociated cells to adherent culture in a culture medium that does not contain a factor selected from the group consisting of GDNF, BDNF and NT-3 using an uncoated culture vessel.

It is another aspect of the present invention is to provide the method as described above, wherein the culture is carried out for not less than 30 days in the step (II).

It is another aspect of the present invention is to provide the method as described above, wherein the culture is carried out for not less than 20 days in the step (IV).

It is another aspect of the present invention is to provide the method as described above, wherein said cell population comprising neurons and astrocytes are produced from pluripotent stem cells by:
 (i) culturing pluripotent stem cells in a culture medium comprising a BMP inhibitor and a TGFβ inhibitor; and
 (ii) culturing the cells obtained in the step (i) in a culture medium comprising a neurotrophic factor.

It is another aspect of the present invention is to provide the method as described above, wherein the step (i) comprises forming an embryoid body/bodies from pluripotent stem cells in a culture medium comprising a BMP inhibitor and a TGFβ inhibitor, and then subjecting the embryoid body/bodies to adherent culture.

It is another aspect of the present invention is to provide the method as described above, wherein said BMP inhibitor is Dorsomorphin and said TGFβ inhibitor is SB431542.

It is another aspect of the present invention is to provide the method as described above, wherein said neurotrophic factor is a factor selected from the group consisting of GDNF, BDNF and NT-3.

It is another aspect of the present invention is to provide the method as described above, wherein the culture is carried out for not less than 66 days in the step (ii).

It is another aspect of the present invention is to provide the method as described above, wherein said cell population comprising neurons and astrocytes is derived from human.

By the method described in the present invention, astrocytes can be produced from neural progenitor cells. Further, using the obtained astrocytes, therapeutic agents for diseases such as astrocytoma, epilepsy, Alexander disease and neurodegeretative diseases can be developed.

Figure 1:
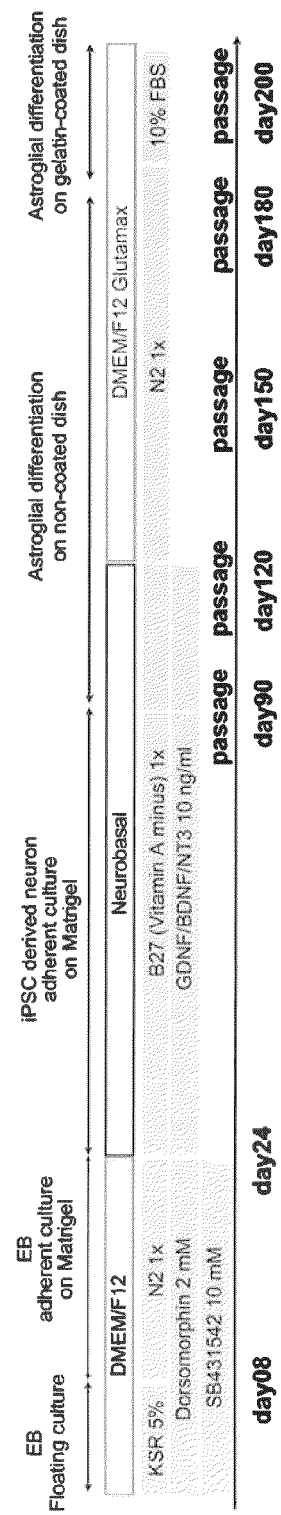
FIG. 1 shows a scheme for producing astrocytes from pluripotent stem cells.

The amount of glutamate decreased with time from an initial concentration of 250 μM represents the uptake of glutamate into the cells.

EMBODIMENTS FOR CARRYING OUT THE INVENTION

The present invention is described below in detail.

The present invention provides a method for producing astrocytes, which method comprises the steps of: (1) culturing neural progenitor cells in a culture medium comprising a neurotrophic factor; (2) dissociating the cells obtained in (1); and (3) subjecting the cells obtained in (2) to adherent culture in a culture medium comprising a neurotrophic factor using an uncoated culture vessel.

In the present invention, the term "neural progenitor cells" means cells that differentiate into neurons or glial cells and express Nestin or NCAM. In the present description, the term "neural progenitor cells" means cells equivalent to neural stem cells, and these two types of cells are not distinguished from each other unless otherwise specified. The term "glial cells" means astrocytes, oligodendrocytes and the like.

Further, in the present invention, the term "astrocytes" means cells that express GFAP or S100β, preferably cells that express GFAP. GFAP is the gene having the sequence of NCBI Accession No. NM_001131019, NM_001242376 or NM_002055.

<Step of Culturing Neural Progenitor Cells in Culture Medium Comprising Neurotrophic Factor>

The culture medium to be used in the step of culturing the neural progenitor cells may be prepared using, as a basal medium, a medium to be used for culturing animal cells. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium and Neurobasal Medium (Life Technologies), and mixtures of these media. The medium is preferably Neurobasal Medium. The medium may contain serum, or may be serum-free. The medium may contain, as required, one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, collagen precursor, trace element, 2-mercaptoethanol and/or 3'-thiolglycerol, and may also contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffer and/or inorganic salt. A preferred medium is Neurobasal Medium supplemented with B27 supplement and Glutamax.

The culture medium to be used for the step of culturing neural progenitor cells preferably comprises a neurotrophic factor. The neurotrophic factor herein means a ligand for a membrane receptor playing an important role for survival and maintenance of functions of motor neurons, and examples of the neurotrophic factor include Nerve Growth Factor (NGF), Brain-derived Neurotrophic Factor (BDNF), Neurotrophin 3 (NT-3), Neurotrophin 4/5 (NT-4/5), Neurotrophin 6 (NT-6), basic FGF, acidic FGF, FGF-5, Epidermal Growth Factor (EGF), Hepatocyte Growth Factor (HGF), Insulin, Insulin Like Growth Factor 1 (IGF 1), Insulin Like Growth Factor 2 (IGF 2), Glia cell line-derived Neurotrophic Factor (GDNF), TGF-b2, TGF-b3, Interleukin 6 (IL-6), Ciliary Neurotrophic Factor (CNTF) and LIF. The neurotrophic factor preferred in the present invention is a factor selected from the group consisting of GDNF, BDNF and NT-3.

In the step of culturing neural progenitor cells, the culture may be carried out using a coated culture vessel. Examples of the coating agent include Matrigel (BD), collagen, gelatin, laminin, heparan sulfate proteoglycan and entactin, and combinations of these agents. The coating agent is preferably Matrigel.

In terms of the culture conditions, the culture temperature is about 30 to 40° C., preferably about 37° C., although the culture temperature is not limited. The culture is carried out in the presence of the atmosphere of air containing $CO_2$, and the $CO_2$ concentration is preferably about 2 to 5%.

The culture period is not limited since long-term culture does not cause any problem, and examples of the culture period include not less than 20 days, not less than 30 days, not less than 40 days, not less than 50 days, not less than 60 days, not less than 70 days, not less than 80 days, not less than 90 days, and periods longer than these. The culture period is preferably not less than 66 days.

The concentration of the above-described neurotrophic factor to be added may be appropriately selected by those skilled in the art in consideration of the effect of the factor, and examples of the concentration include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 30 ng/ml, 40 ng/ml, 50 ng/ml, 60 ng/ml, 70 ng/ml, 80 ng/ml, 90 ng/ml and 100 ng/ml. The concentration is preferably 10 ng/ml.

<Step of Dissociating Cells>

In the step of dissociating the cells, cells adhering to each other and forming a population are dissociated (separated) into individual cells.

Examples of the method for dissociating the cells include a method in which the cells are mechanically dissociated, and a method in which a dissociation solution having the protease activity and the collagenase activity (e.g., Accutase™ or Accumax™) or a dissociation solution having only the collagenase activity is used. The method is preferably a method in which a dissociation solution having the protease activity and the collagenase activity (especially preferably Accutase™) is used to dissociate human pluripotent stem cells.

<Step of Subjecting Dissociated Cells to Adherent Culture in Culture Medium Comprising Neurotrophic Factor Using Uncoated Culture Vessel>

The uncoated culture vessel means a dish, plate or flask for cell culture that are widely used by those skilled in the art, which vessel has an arbitrary shape and has not been subjected to a treatment process using a coating agent before use in the culture. The vessel is preferably a polystyrene culture vessel. Examples of the coating agent include Matrigel (BD), collagen, gelatin, laminin, heparan sulfate proteoglycan and entactin, and, in this step, it is preferred to use a culture vessel that has not been treated with at least these coating agents.

In the culture after dissociation of cells, the same culture medium comprising a neurotrophic factor as described above can be used. The culture period is not limited since long-term culture does not cause a problem, and examples of the culture period include not less than 5 days, not less than 10 days, not less than 15 days, not less than 20 days, not less than 25 days, not less than 30 days, not less than 35 days, not less than 40 days, not less than 45 days, not less than 50 days, and periods longer than these. The culture period is preferably not less than 30 days.

<Additional Step>

In the present invention, the production of astrocytes may be carried out by further dissociating the obtained cells and subjecting the dissociated cells to adherent culture using an uncoated culture vessel, in a culture medium that does not contain a factor selected from the group consisting of GDNF, BDNF and NT-3. The dissociation of cells can be carried out by the same method as described above, and the dissociation is preferably carried out using a dissociation solution having the protease activity and the collagenase activity.

The culture medium that does not contain a factor selected from the group consisting of GDNF, BDNF and NT-3 can be prepared using, as a basal medium, a medium to be used for culturing animal cells. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium and Neurobasal Medium (Life Technologies), and mixtures of these media. The medium is preferably Neurobasal Medium. The medium may contain serum, or may be serum-free. The medium may contain, as required, one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, collagen precursor, trace element, 2-mercaptoethanol and/or 3'-thiolglycerol, and may also contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffer and/or inorganic salt. A preferred medium that does not contain a factor selected from the group consisting of GDNF, BDNF and NT-3 is DMEM/F12 containing N2 supplement and Glutamax, and DMEM/F12 containing serum and Glutamax.

The period of this step is not limited since long-term culture does not cause a problem, and examples of the culture period include not less than 5 days, not less than 10 days, not less than 15 days, not less than 20 days, not less than 25 days, not less than 30 days, not less than 35 days, not less than 40 days, not less than 45 days, not less than 50 days, and periods longer than these. The period is preferably not less than 20 days or not less than 30 days.

In terms of the culture conditions in this step, the culture temperature is about 30 to 40° C., preferably about 37° C., although the culture temperature is not limited. The culture is carried out in the presence of the atmosphere of air containing $CO_2$, and the $CO_2$ concentration is preferably about 2 to 5%.

The step of cell dissociation and culture of the dissociated cells is preferably carried out at least once for increasing the efficiency of obtaining astrocytes. The step of cell dissociation and culture of the dissociated cells is preferably repeated not less than twice, not less than 3 times, not less than 4 times or not less than 5 times. The step is preferably repeated 3 times.

<Method for Selecting. Astrocytes>

After the step of culturing neural progenitor cells in a culture medium containing a neurotrophic factor, neurons, in addition to astrocytes, may be produced at the same time. However, since astrocytes are more likely to adhere to uncoated culture vessels as compared to neurons, use of the method of the present invention allows selective acquisition of astrocytes at high efficiency from a cell population comprising astrocytes and neurons. Therefore, the present invention provides a method for selectively culturing astrocytes from a cell population comprising astrocytes and neurons. More specifically, the method comprises the step of separating the cells described above and a step of culturing the cells using an uncoated culture vessel.

<Culture and Storage of Astrocytes>

The astrocytes produced by the method of the present invention can be cultured using a gelatin-coated culture vessel, in the above-described culture liquid that does not contain a factor selected from the group consisting of GDNF, BDNF and NT-3.

In terms of the culture conditions, the culture is carried out at a temperature of about 30 to 40° C., preferably about 37° C. in the atmosphere of air containing $CO_2$. The $CO_2$ concentration is preferably about 2 to 5%.

The astrocytes produced by the method of the present invention may be stored in a cryopreservation solution at a low temperature, for example, not more than −80° C. or not more than −196° C. The cryopreservation solution to be used at this time is not limited, and may be physiological saline or phosphate buffered saline supplemented with a biological material(s) such as glucose, serum and/or albumin, and/or DMSO, glycerol, polysaccharide and/or polyphenol.

<Production of Neural Progenitor Cells>

The neural progenitor cells may be either neural progenitor cells isolated from a living body, or cells induced from another cell species in vitro. The neural progenitor cells are preferably neural progenitor cells obtained by differentiation induction of pluripotent stem cells.

The differentiation induction of pluripotent stem cells into neural progenitor cells may be carried out using a method well known to those skilled in the art, and the method of differentiation induction is not limited. Examples of the method include: (1) a method in which embryoid bodies are formed in a serum-free medium, followed by allowing differentiation (SFEB method) (Watanabe K, et al. Nat Neurosci. 8:288-96, 2005); (2) a method in which ES cells are cultured on stromal cells to cause differentiation (SDIA method) (Kawasaki H, et al. Neuron. 28:31-40, 2000); and (3) a method in which an agent is added onto Matrigel to perform culture (Chambers S M, et al. Nat Biotechnol. 27:275-80, 2009). The method of differentiation induction of pluripotent stem cells into neural progenitor cells may be preferably a method comprising the step of culturing pluripotent stem cells in a culture medium comprising a BMP inhibitor and a TGFβ inhibitor.

As a preferred method for differentiation induction of pluripotent stem cells into neural progenitor cells, pluripotent stem cells may be separated by an arbitrary method, and cultured by suspension culture or adherent culture using a coated culture vessel. The pluripotent stem cells are preferably subjected to suspension culture followed by adherent culture. Examples of the method of separation of human pluripotent stem cells herein include a method by mechanical separation, and a separation method using a separation solution having the protease activity and the collagenase activity (e.g., Accutase™ or Accumax™) or a separation solution having only the collagenase activity. The method is preferably a method in which human pluripotent stem cells are dissociated using a separation solution having the protease activity and the collagenase activity (especially preferably Accutase™), followed by mechanically and finely dispersing the dissociated cells into single cells. The human pluripotent stem cells to be used herein are preferably in the form of colonies cultured to 80% confluence with respect to the dish used.

The suspension culture means culturing of cells in a state where the cells are not adhering to the culture vessel. The culture vessel that may be used is not limited, and examples of the culture vessel include culture vessels that are not artificially treated for the purpose of enhancing adhesiveness to cells (for example, by coating treatment with an extracellular matrix or the like), and culture vessels that are artificially treated such that adhesion is artificially suppressed (for example, by coating treatment with polyhydroxyethylmethacrylate (poly-HEMA)) or with a nonionic surfactant polyol (e.g., Pluronic F-127)).

In the adherent culture, the cells are cultured in an arbitrary medium in a coated culture vessel. Examples of the coating agent include Matrigel (BD), collagen, gelatin, laminin, heparan sulfate proteoglycan and entactin, and combinations of these agents. The coating agent is preferably Matrigel.

The medium in this step may be prepared using, as a basal medium, a medium to be used for culturing animal cells. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium and Neurobasal Medium (Life Technologies), and mixtures of these media. The medium is preferably DMEM/F12 medium supplemented with equal amounts of DMEM and Ham's F12 medium. The medium may contain serum, or may be serum-free. The medium may contain, as required, one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, collagen precursor, trace element, 2-mercaptoethanol and/or 3'-thiolglycerol, and may also contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffer and/or inorganic salt. The medium is preferably DMEM/F12 medium containing KSR, amino acids and L-glutamic acid, or DMEM/F12 medium containing N2 supplement, KSR, amino acids and L-glutamine.

In the present invention, a BMP inhibitor and a TGFβ inhibitor are preferably added to the medium. The BMP inhibitor herein means a low-molecular-weight inhibitor involved in inhibition of BMP signaling that mediates binding of BMP (bone morphogenetic protein) to a BMP receptor (type I or type II), and is different from natural inhibitors such as Noggin, chordin and follistatin, which are protein-based inhibitors. This inhibitor should have an action to cause differentiation induction of pluripotent stem cells into neural progenitor cells. Examples of low-molecular-weight BMP inhibitors having such a property include compounds that inhibit BMP2, BMP4, BMP6 or BMP7, which have a capacity to activate a transcription factor SMAD1, SMAD5 or SMAD8, and examples of the compounds include Dorsomorphin (that is, 6-[4-(2-piperidin-1-yl-ethoxy)phenyl]-3-pyridin-4-yl-pyrazolo[1,5-a]pyrimidine) and its derivatives (P. B. Yu et al. (2007), Circulation, 116:II_60; P. B. Yu et al. (2008), Nat. Chem. Biol., 4:33-41; J. Hao et al. (2008), PLoS ONE (www.plozone.org), 3(8):e2904). Dorsomorphin is commercially available, and can be obtained from, for example, Sigma-Aldrich. Dorsomorphin has a biological activity that inhibits the above-described BMP signaling by inhibition of binding of BMP to a BMP receptor. Other examples of the inhibitor include BMP I-type receptor kinase inhibitors such as LDN-193189 (that is, 4-(6-(4-(piperazin-1-yl)phenyl)pyrazolo[1,5-a]pyrimidin-3-yl)quinoline) and its derivatives (Yu P B et al. Nat Med, 14:

1363-9, 2008). LDN-193189 is commercially available, and can be obtained from Stemgent, Inc. and the like In cases where the BMP inhibitor is, for example, Dorsomorphin, examples of its concentration in the medium include 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 10 mM, 20 mM, 30 mM, 40 mM, 50 mM and 100 mM. The concentration is preferably 2 mM.

The TGFβ inhibitor is a low-molecular-weight inhibitor that interferes with signaling by the TGFβ family, and examples of the TGFβ inhibitor include SB431542 and SB202190 (these are described in R. K. Lindemann et al., Mol. Cancer 2:20(2003)), SB505124 (GlaxoSmithKline), NPC30345, SD093, SD908, SD208 (Scios), LY2109761, LY364947 and LY580276 (Lilly Research Laboratories). SB431542 is preferred.

In cases where the TGFβ inhibitor is SB431542, examples of its concentration in the medium include 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM and 100 mM. The concentration is preferably 10 mM.

The culture temperature is about 30 to 40° C., preferably about 37° C., although the culture temperature is not limited. The culture is carried out in the presence of the atmosphere of air containing $CO_2$. The $CO_2$ concentration is preferably about 2 to 5%, preferably 5%. The culture period is at least 20 days, and examples of the culture period include 21 days, 24 days, 27 days, 30 days, 33 days, 36 days, 39 days and 42 days. The culture period is preferably 24 days.

<Pluripotent Cells>

The pluripotent stem cells that can be used in the present invention are stem cells having pluripotency that allows differentiation into any kind of cells present in a living body, which stem cells also have the growth ability. Examples of the pluripotent stem cells include embryonic stem (ES) cells, embryonic stem (ntES) cells derived from a cloned embryo obtained by nuclear transfer, germline stem cells ("GS cells"), embryonic germ cells ("EG cells"), induced pluripotent stem (iPS) cells, and pluripotent cells derived from cultured fibroblasts or bone marrow stem cells (Muse cells). In view of obtaining stem cells without destruction of the embryo, iPS cells or Muse cells are preferably used in the present invention.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst which is the embryo formed following the 8-cell stage and the morula stage of a fertilized egg, and ES cells have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292:154-156), and this was followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of the subject animal, followed by culturing the inner cell mass on fibroblasts as feeders. The cells can be maintained by subculturing using a medium supplemented with substances such as leukemia inhibitory factor (LIF) and/or basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science: 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

In terms of the culture medium for preparation of ES cells, human ES cells can be maintained using, for example, DMEM/F-12 culture medium supplemented with 0.1 mM 2-mercaptoethanol, 0.1 mM non-essential amino acids, 2 mM L-glutamic acid, 20% KSR and 4 ng/ml bFGF at 37° C. under a moist atmosphere of 5% $CO_2$ (H. Suemori et al. (2006), Biochem. Biophys. Res. Commun., 345:926-932). The ES cells need to be subcultured every 3 to 4 days, and the subculture can be carried out using, for example, 0.25% trypsin and 0.1 mg/ml collagenase IV in PBS supplemented with 1 mM $CaCl_2$ and 20% KSR.

Selection of ES cells can be generally carried out by the Real-Time PCR method using as an index/indices expression of a gene marker(s) such as alkaline phosphatase, Oct-3/4 and/or Nanog. In particular, for selection of human ES cells, expression of a gene marker(s) such as OCT-3/4, NANOG and/or ECAD can be used as an index/indices (E. Kroon et al. (2008), Nat. Biotechnol., 26:443-452).

For example, in terms of human ES cell lines, WA01(H1) and WA09(H9) can be obtained from WiCell Research Institute, and KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al: (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similar to ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing specific reprogramming factors to somatic cells, which reprogramming factors are in the forms of DNAs or proteins. iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007), Cell, 131:861-872; J. Yu et al. (2007), Science, 318:1917-1920;

Nakagawa, M. et al., Nat. Biotechnol. 26:101-106 (2008); WO 2007/069666). The reprogramming factors may be constituted by genes or gene products thereof, or non-coding RNAs, which are expressed specifically in ES cells; or genes or gene products thereof, non-coding RNAs or low molecular weight compounds, which play important roles in maintenance of the undifferentiated state of ES cells. Examples of the genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3 and Glis1, and these reprogramming factors may be used either alone or in combination. Examples of the combinations of the reprogramming factors include those described in WO2007/069666; WO2008/118820; WO2009/007852; WO2009/032194; WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/111409; WO 2010/111422; WO2010/115050; WO2010/124290; WO2010/147395; WO2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474:225-9.

Examples of the above-described reprogramming factors include histone deacetylase (HDAC) inhibitors [for example, low molecular weight inhibitors such as valproic acid (VPA), trichostatin A, sodium butyrate, MC 1293 and M344; and nucleic acid-type expression inhibitors such as siRNAs and shRNAs against HDAC (e.g., HDAC1 siRNA Smartpool (Millipore) and HuSH 29mer shRNA Constructs against HDAC1 (OriGene))], MEK inhibitors (for example, PD184352, PD98059, U0126, SL327 and PD0325901), Glycogen synthase kinase-3 inhibitors (for example, Bio and CHIR99021), DNA methyltransferase inhibitors (for example, 5'-azacytidine), histone methyltransferase inhibitors (for example, low molecular weight inhibitors such as BIX-01294; and nucleic acid-type expression inhibitors such as siRNAs and shRNAs against Suv39h1, Suv39h2, SetDB1 and G9a), L-channel calcium agonists (for example, Bayk8644), butyric acid, TGFβ inhibitors or ALK5 inhibitors (for example, LY364947, SB431542, 616453 and A-83-01), p53 inhibitors (for example, siRNAs and shRNAs against p53), ARID3A inhibitors (for example, siRNAs and shRNAs against ARID3A), miRNAs such as miR-291-3p, miR-294, miR-295 and mir-302, Wnt Signaling (for example, soluble Wnt3a), neuropeptide Y, prostaglandins (for example, prostaglandin E2 and prostaglandin J2), hTERT, SV40LT, UTF1, IRX6, GLIS1, PITX2 and DMRTB1, which are employed for enhancing the establishment efficiency, and, in the present description, these factors employed for the purpose of enhancement of the establishment efficiency are not particularly distinguished from reprogramming factors.

In cases where the reprogramming factors are in the form of protein, each reprogramming factor may be introduced into somatic cells by a method such as lipofection, fusion with a cell-permeable peptide (e.g., HIV-derived TAT or polyarginine), or microinjection.

In cases where the reprogramming factors are in the form of DNA, each reprogramming factor may be introduced into somatic cells by a method such as use of a vector including virus, plasmid and artificial chromosome vectors; lipofection; use of liposome; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (WO 2010/008054). Examples of the artificial chromosome vector include human artificial chromosome (HAC), yeast artificial chromosome (YAC), and bacterial artificial chromosome (BAC and PAC). Examples of the plasmid which may be used include plasmids for mammalian cells (Science, 322:949-953, 2008). The vectors may contain a regulatory sequence(s) such as a promoter, enhancer, ribosome binding sequence, terminator and/or polyadenylation site; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; and/or the like to enable expression of the nuclear reprogramming factors. Further, in order to remove, after introduction of the above vector into somatic cells, the genes encoding the reprogramming factors, or both the promoters and the genes encoding the reprogramming factors linked thereto, the vector may have LoxP sequences upstream and downstream of these sequences.

Further, in cases where the reprogramming factors are in the form of RNA, each reprogramming factor may be introduced into somatic cells by a method such as lipofection or microinjection, and an RNA into which 5-methylcytidine and pseudouridine (TriLink Biotechnologies) were incorporated may be used in order to suppress degradation (Warren L, (2010) Cell Stem Cell. 7:618-630).

Examples of the medium for induction of the iPS cells include the DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the culture method include a method wherein somatic cells and reprogramming factors are brought into contact with each other at 37° C. in the presence of 5% CO$_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in the DMEM medium supplemented with 10% FBS (this medium may further contain LIF, penicillin/streptomycin, puromycin, L-glutamine, non-essential amino acids, β-mercaptoethanol and/or the like, as appropriate) for about 25 to about 30 days or longer, thereby allowing ES-like colonies to appear. Preferred examples of the culture method include a method wherein the somatic cells themselves to be reprogrammed are used instead of the feeder cells (Takahashi K, et al. (2009), PLoS One. 4:e8067 or WO2010/137746), and a method wherein an extracellular matrix (e.g., Laminin-5 (WO2009/123349) or Matrigel (BD)) is used instead.

Other examples include a method wherein the culture is carried out using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of not less than 0.1% and not more than 15%) (Yoshida Y, et al. (2009), Cell Stem Cell. 5:237-241 or WO2010/013845).

During the culture, the medium is replaced with a fresh medium once every day from Day 2 of the culture. The number of the somatic cells used for nuclear reprogramming is not restricted, and usually within the range of about $5 \times 10^3$ to about $5 \times 10^6$ cells per 100-$cm^2$ area on the culture dish.

iPS cells may be selected based on the shape of each formed colony. In cases where a drug resistance gene which is expressed in conjunction with a gene that is expressed upon reprogramming of a somatic cell (e.g., Oct3/4 or Nanog) was introduced as a marker gene, established iPS cells can be selected by culturing the cells in a medium containing the corresponding drug (selection medium). Further, iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means any animal cells (preferably cells of mammals including human) excluding germ-line cells and totipotent cells such as eggs, oocytes and ES cells. Examples of the somatic cells include, but are not limited to, any of fetal somatic cells, neonatal somatic cells, and mature, healthy and diseased somatic cells, as well as any of primary cultured cells, subcultured cells and established cell lines. Particular examples of the somatic cells include (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and adipocytes.

In cases where iPS cells are used as a material for cells to be transplanted, somatic cells whose HLA genotype is the same or substantially the same as that of the individual to which the cells are to be transplanted are preferably used in view of prevention of the rejection reaction. Here, "substantially the same" means that the HLA genotype is matching to an extent at which the immune reaction against the transplanted cells can be suppressed with an immunosuppressive agent. For example, the somatic cells have matched HLA types at 3 loci HLA-A, HLA-B and HLA-DR, or at 4 loci further including HLA-C.

(E) ES Cells Derived from Cloned Embryo Obtained by Nuclear Transfer ntES cells are ES cells derived from a cloned embryo prepared by the nuclear transfer technique, and have properties which are almost the same as those of ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique is employed (Sayaka Wakayama et al. (2008), Experimental Medicine 26(5) (extra edition):47-52). In nuclear transfer, reprogramming can be achieved by injecting the nucleus of a somatic cell into a mammalian enucleated unfertilized egg and culturing the resultant for several hours.

(F) Multilineage-Differentiating Stress Enduring Cells (Muse Cells)

Muse cells are pluripotent stem cells produced by the method described in WO2011/007900. More specifically, Muse cells are pluripotent cells positive for SSEA-3 and CD105, obtained by subjecting fibroblasts or bone marrow stromal cells to trypsin treatment for a long time, preferably for 8 hours or 16 hours, and then to suspension culture.

<Astrocytes>

In the present invention, the astrocytes prepared by the above-described differentiation induction method can be identified by staining with an arbitrary marker(s) such as GFAP, and purified by a method well known to those skilled in the art.

The thus obtained astrocytes can be used for screening of therapeutic agents for astrocytoma, epilepsy, Alexander disease and neurodegeretative diseases. Examples of the neurodegeretative diseases include amyotrophic lateral sclerosis (ALS), Parkinson's disease, Alzheimer-type dementia, progressive supranuclear palsy (PSP), Huntington disease, multiple system atrophy (MSA) and spinocerebellar degeneration (SCD).

<Kit for Differentiation Induction of Neural Progenitor Cells into Astrocytes>

The present invention provides a kit for differentiation induction of neural progenitor cells into astrocytes. The kit may comprise a growth factor, compound, culture medium, dissolution solution, and/or coating agent for a culture vessel. The kit may further comprise a document or an instruction that describes a procedure for differentiation induction.

EXAMPLES iPS Cells

From explants obtained from two healthy individuals by 3-mm skin biopsy with patients' consent, human dermal fibroblasts (HDFs) were established. Into the established HDFs, human cDNAs (SOX2, KLF4, OCT4, L-MYC and LIN28) and p53 shRNA were introduced using an episomal vector according to the method of Okita et al. (Okita et al., Nat Methods. 2011, 8, 409-412). Several days after the introduction, the HDFs were recovered, and plated again onto an SNL feeder cell layer. On the next day, the medium was replaced with a medium for primate embryonic stem cells (Reprocell, Kanagawa, Japan) supplemented with 4 ng/ml bFGF (Wako Chemicals, Osaka, Japan). The medium was replaced every other day. Thirty days after the introduction of cDNAs, a colony of iPS cells was selected from each sample (N116213 and N117322). Further, cells established by Okita et al. were received (409B2). Thus, a total of 3 kinds of iPS cells were used for the Examples shown below.

Differentiation Induction into Astrocytes
1. Induction of Neural Progenitor Cells The feeder cells cocultured with the iPS cells obtained by the above method were selectively detached using CTK solution (ReproCell), and the remaining iPS cells were dissociated with Accutase (Innovative Cell Technologies). The dissociated iPS cells were suspended in DFK 5% medium (DMEM/Ham's F12 (Gibco) supplemented with 5% KSR (Invitrogen), L-glutamine (Sigma-Aldrich) and 0.1 M 2-mercaptoethanol (Invitrogen)) supplemented with 2 µM Dorsomorphin (Sigma-Aldrich) and 10 µM SB431542 (Cayman Chemical), and then plated in a U-bottom 96-well plate coated with 2% Pluronic F-127 (Sigma-Aldrich) solution in ethanol, to allow formation of embryoid bodies (EBs), followed by performing suspension culture for 8 days. Subsequently, the obtained EBs were transferred to a 6-well plate coated with Matrigel (BD), and cultured for 16 days by adherent culture in DFK 5% medium supplemented with 1×N2 supplement (Invitrogen), 2 µM Dorsomorphin and 10 µM SB431542 (24 days of culture in total), to obtain neural progenitor cells.

2. Induction of Astrocytes

The neural progenitor cells obtained by the above method were dissociated using Accutase (Innovative Cell Technologies), and cultured for 66 days by adherent culture in Neurobasal medium (Invitrogen) supplemented with 1×B27 without Vitamin A (Invitrogen), 1× Glutamax (Invitrogen), 10 ng/ml BDNF, 10 ng/ml GDNF and 10 ng/ml NT-3 using a Matrigel-coated 12-well plate (90 days of culture in total). Subsequently, the obtained cells were dissociated using Accutase and transferred to an uncoated 6-cm dish, followed by performing adherent culture for 30 days in Neurobasal medium supplemented with 1×B27 without Vitamin A, 1× Glutamax, 10 ng/ml BDNF, 10 ng/ml GDNF and 10 ng/ml NT-3 (120 days of culture in total). The cells without adhesion at this time died by anoikis. The cells adhered were dissociated using Accutase, and transferred to an uncoated 6-cm dish, followed by performing adherent culture for 30 days in DMEM/F12, Glutamax (Invitrogen) supplemented with 1×N2 supplement (150 days of culture in total). Further, the cells obtained twice were dissociated, and cultured for 30 days under the same conditions, to obtain astrocytes (200 days of culture in total). Thereafter, in the cases where the cells were to be used for a glutamine uptake test, the obtained cells were dissociated and transferred to a 6-cm dish coated with 0.1% gelatin, followed by performing culture in DMEM/F12, Glutamax supplemented with 1×N2 supplement. These steps are shown in FIG. 1.

Evaluation of Astrocytes
1. Microarray Analysis

Figure 2:
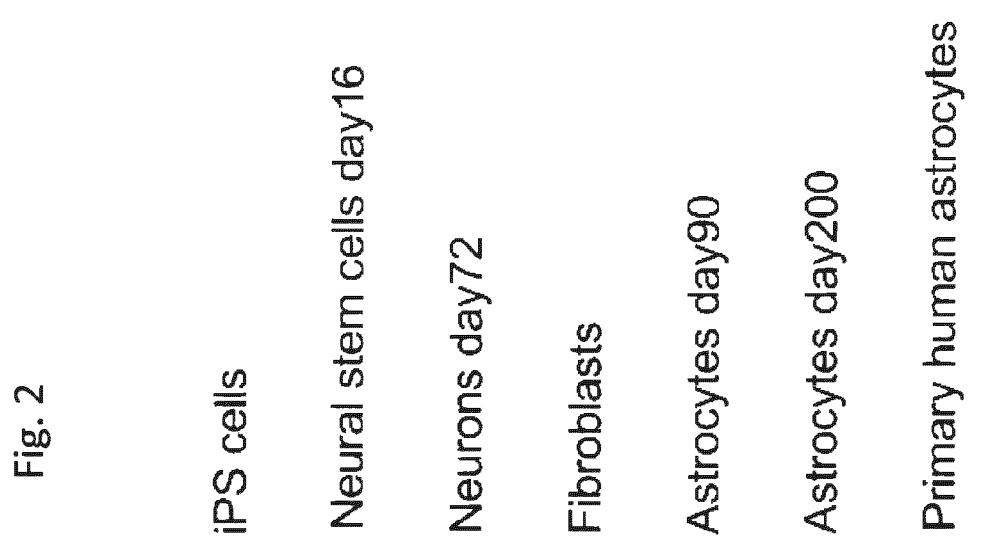
FIG. 2 shows the results (photographs) obtained by hierarchical cluster analysis of the gene expression pattern of each type of cells using a microarray.

Total RNA was extracted from the astrocytes obtained by the above-described method (astrocytes obtained on Day 90 of culture or on Day 200 of culture) and primary astrocytes (Lonza) using RNeasy mini kit (Qiagen), and fragmented and converted into biotin-labeled cDNAs using Ovation Pico WTA System/Encore Biotin Module kit (NuGENE). The obtained cDNA sample was subjected to hybridization using GeneChip Human Gene 1.0 ST Array (Affymetrix) and then scanning with G2565BA Microarray Scanner System (Agilent). The data obtained after scanning were analyzed using GeneSpring GX 7.3.1 software (Agilent). The results of the thus performed cluster analysis are shown in FIG. 2. From these results, it was confirmed that, in the above-described method for inducing astrocytes, the astrocytes obtained on Day 200 are closer to the primary astrocytes, as compared to the astrocytes obtained on Day 90.

2. Immunostaining

Figure 3:
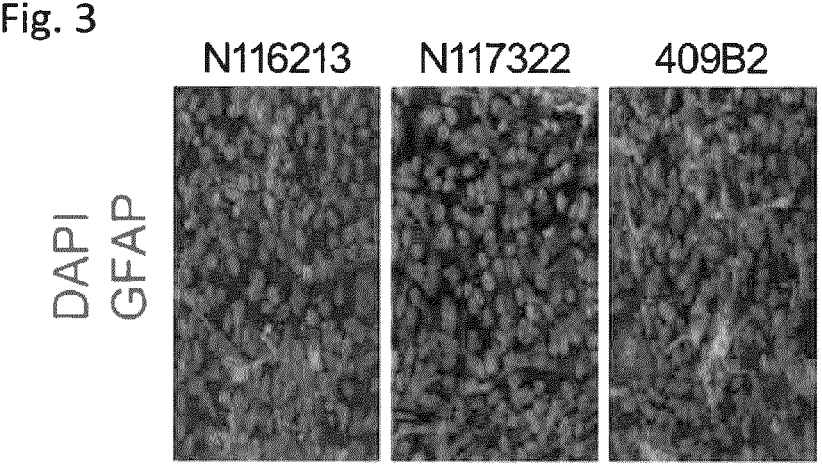
FIG. 3 shows immunostaining images (photographs) of astrocytes obtained by differentiation induction of each type of human iPS cells. In this figure, the blue areas indicate images of nuclei stained with DAPI, and the red areas indicate stained images produced by a GFAP antibody.
Figure 4:
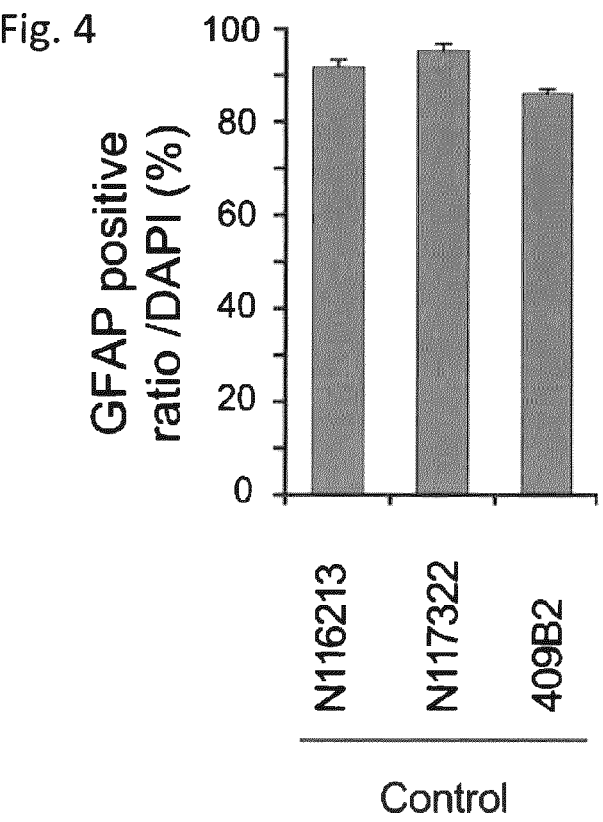
FIG. 4 shows the content of GFAP-positive cells among astrocytes produced by differentiation induction of each type of human iPS cells.

The astrocytes obtained by the above-described method were fixed by being left to stand at room temperature for 30 minutes in 4% paraformaldehyde (pH 7.4). The astrocytes were then washed with PBS supplemented with 0.2% Triton X-100, and blocked with PBS supplemented with 10% donkey serum. The reaction was allowed to proceed with GFAP antibody (Dako) (1:2000 dilution) at 4° C. overnight, and staining was then carried out with a fluorescence-labeled secondary antibody and DAPI. The stained images are shown in FIG. 3. The ratio of the number of GFAP-positive cells to DAPI-stained cells at this time is shown in FIG. 4. From the obtained results, it was confirmed that about 90% of the obtained astrocytes were GFAP-positive cells.

3. Glutamine Uptake Test

Figure 5:
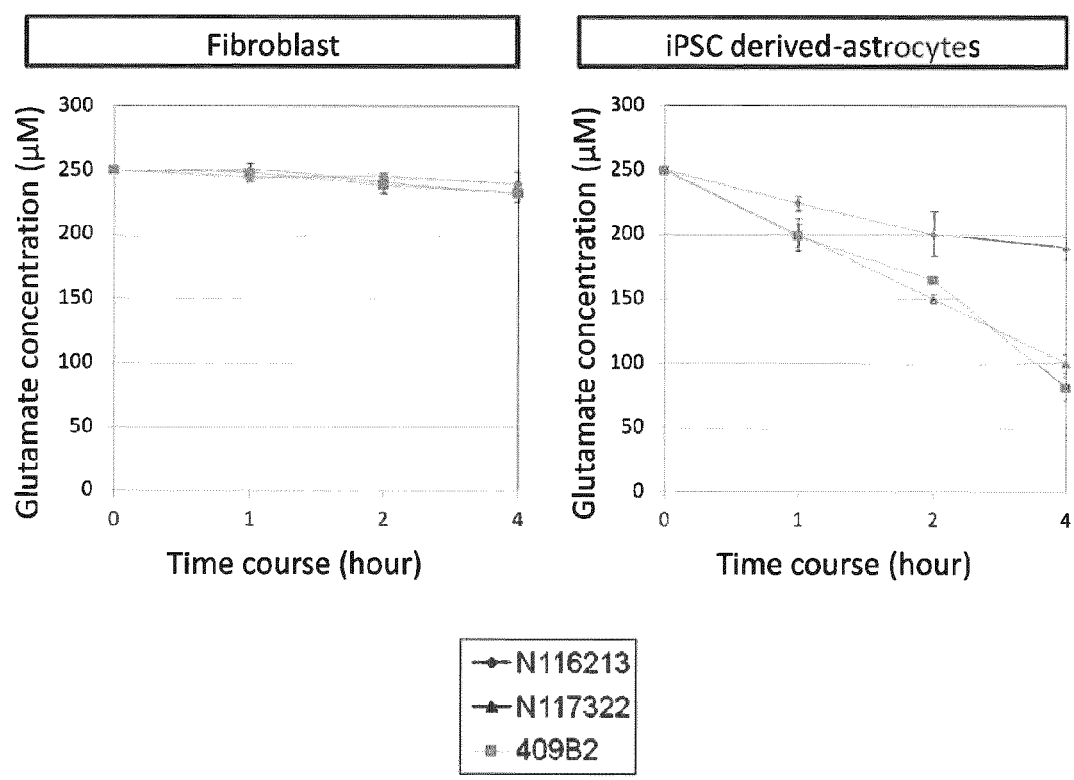
FIG. 5 shows the capacity of fibroblasts (left panel), or astrocytes obtained by differentiation induction of human iPS cells (right panel), to take up glutamate in the medium.

To each well of a 48-well plate coated with 0.1% gelatin, $4 \times 10^4$ astrocytes obtained by the above-described method were transferred, and the astrocytes were cultured for 3 days. Thereafter, L-glutamate (Nacalai) was added to the cells such that the final concentration was 250 µM, and the extracellular concentration of glutamate was measured using Glutamate Assay Kit colorimetric assay II (Yamasa Corporation). By this, the uptake of glutamate into the cells with time was measured/calculated. The results are shown in FIG. 5. The obtained astrocytes were confirmed to have the capacity to take up glutamate.

Thus, it was confirmed that functional astrocytes can be obtained from iPS cells by the above method.

What is claimed is:

1. A method for producing astrocytes, comprising the steps:
   (1) culturing human neural progenitor cells in a culture medium comprising neurotrophic factors consisting of GDNF, BDNF and NT-3;
   (2) dissociating the cells obtained in step (1); and
   (3) subjecting the cells obtained in step (2) to adherent culture in a culture medium comprising neurotrophic factors consisting of GDNF, BDNF and NT-3 using an uncoated culture vessel.

2. The method according to claim 1, further comprising the steps:
   (4) dissociating the cells obtained in step (3); and
   (5) subjecting the cells obtained in step (4) to adherent culture in a culture medium that does not contain a factor selected from the group consisting of GDNF, BDNF and NT-3 using an uncoated culture vessel.

3. The method according to claim 2, further comprising repeating, at least twice, dissociating the cells obtained in step (5) and then subjecting the dissociated cells to adherent culture in a culture medium that does not contain a factor selected from the group consisting of GDNF, BDNF and NT-3 using an uncoated culture vessel.

4. The method according to claim 2, further comprising the steps:
   (6) dissociating the cells obtained in step (5); and
   (7) subjecting the cells obtained in step (6) to adherent culture in a culture medium that does not contain a factor selected from the group consisting of GDNF, BDNF and NT-3 using a gelatin-coated culture vessel.

5. The method according to claim 2, wherein the culture is carried out for not less than 20 days in step (5).

6. The method according to claim 1, wherein the culture is carried out for not less than 66 days in step (1).

7. The method according to claim 1, wherein the culture is carried out for not less than 30 days in step (3).

8. A method for selectively culturing astrocytes in a human cell population comprising neurons and astrocytes, comprising:
(I) dissociating the human cell population; and
(II) subjecting the cells obtained in the step (I) to adherent culture in a culture medium comprising neurotrophic factors consisting of GDNF, BDNF and NT-3 using an uncoated culture vessel.

9. The method according to claim 8, further comprising:
(III) dissociating the cells obtained in step (II); and
(IV) subjecting the cells obtained in step (III) to adherent culture in a culture medium that does not contain a factor selected from the group consisting of GDNF, BDNF and NT-3 using an uncoated culture vessel.

10. The method according to claim 9, further comprising repeating, at least twice, dissociating the cells obtained in step (IV) and then subjecting the dissociated cells to adherent culture in a culture medium that does not contain a factor selected from the group consisting of GDNF, BDNF and NT-3 using an uncoated culture vessel.

11. The method according to claim 9, wherein the culture is carried out for not less than 20 days in step (IV).

12. The method according to claim 8, wherein the culture is carried out for not less than 30 days in step (II).

13. A method for selectively culturing astrocytes in a cell population comprising neurons and astrocytes, comprising:
(i) culturing human pluripotent stem cells in a culture medium comprising a BMP inhibitor and a TGFβ inhibitor;
(ii) culturing the cells obtained in step (i) in a culture medium comprising neurotrophic factors consisting of GDNF, BDNF and NT-3 to obtain a cell population comprising neurons and astrocytes;
(iii) dissociating the cell population of step (ii); and
(iv) subjecting the cells obtained in step (iii) to adherent culture in a culture medium comprising neurotrophic factors consisting of GDNF, BDNF and NT-3 using an uncoated culture vessel to selectively culture astrocytes.

14. The method according to claim 13, wherein step (i) comprises forming an embryoid body/bodies from pluripotent stem cells in a culture medium comprising a BMP inhibitor and a TGFβ inhibitor, and then subjecting the embryoid body/bodies to adherent culture.

15. The method according to claim 13, wherein said BMP inhibitor is Dorsomorphin and said TGFβ inhibitor is SB431542.

16. The method according to claim 13, wherein the culture is carried out for not less than 66 days in step (ii).

* * * * *